United States Patent
Frushour

(10) Patent No.: US 11,207,122 B2
(45) Date of Patent: Dec. 28, 2021

(54) SYSTEM, APPARATUS, AND METHOD FOR POWERING A BIPOLAR ENERGY CONTROLLER

(71) Applicant: COVIDIEN LP, Mansfield, MA (US)

(72) Inventor: Scott E. M. Frushour, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 740 days.

(21) Appl. No.: 16/071,948

(22) PCT Filed: Aug. 4, 2017

(86) PCT No.: PCT/CN2017/096062
§ 371 (c)(1),
(2) Date: Jul. 23, 2018

(87) PCT Pub. No.: WO2019/024097
PCT Pub. Date: Feb. 7, 2019

(65) Prior Publication Data
US 2021/0204997 A1 Jul. 8, 2021

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1445* (2013.01); *A61B 2018/00702* (2013.01);
(Continued)

(58) Field of Classification Search
CPC ............ A61B 18/1206; A61B 18/1445; A61B 2018/00702; A61B 2018/00845;
(Continued)

(56) References Cited

U.S. PATENT DOCUMENTS 5,759,158 A * 6/1998 Swanson ................ A61B 5/287
600/508
2004/0030328 A1 2/2004 Eggers et al.
(Continued)

FOREIGN PATENT DOCUMENTS

CN 203408099 U 1/2014
CN 204192735 U 3/2015

OTHER PUBLICATIONS

Notification of Transmittal of the International Seach Report and the Written Opinion of the International Searching Authority, or the Declaration issued in corresponding PCT Application No. PCT/CN2017/096062 dated Apr. 28, 2018, 10 pages.

*Primary Examiner* — Daniel W Fowler

(57) ABSTRACT

A power device is configured couple to an electrosurgical generator (410). The power device includes at least one connector (420, 422, 423, 510, 511), a rectifier (113), an energy storage device (115), and a bipolar energy controller (101). The at least one connector (420, 422, 423, 510, 511) is configured to couple to the electrosurgical generator (410) and receive electrosurgical energy. The rectifier (113) is configured to rectify at least a portion of the electrosurgical energy and provide rectified energy. The energy storage device (115) is configured to store at least a portion of the rectified energy. The bipolar energy controller (101) is configured to be powered by the energy storage device (115) and to control providing of an output bipolar energy.

14 Claims, 8 Drawing Sheets

(52) U.S. Cl.
CPC .............. *A61B 2018/00845* (2013.01); *A61B 2018/00869* (2013.01); *A61B 2018/126* (2013.01); *A61B 2018/1253* (2013.01)

(58) Field of Classification Search
CPC ...... A61B 2018/1253; A61B 2018/126; A61B 2018/00869
See application file for complete search history.

(56) References Cited

U.S. PATENT DOCUMENTS

| | | | |
|---|---|---|---|
| 2008/0208185 A1* | 8/2008 | Fischer | A61B 18/1206 606/37 |
| 2013/0178852 A1 | 7/2013 | Allen, IV et al. | |
| 2013/0345695 A1* | 12/2013 | McPherson | H01Q 1/248 606/34 |
| 2015/0190189 A1 | 7/2015 | Yates et al. | |

* cited by examiner

SYSTEM, APPARATUS, AND METHOD FOR POWERING A BIPOLAR ENERGY CONTROLLER

FIELD OF THE INVENTION

The present disclosure relates to systems, apparatuses, and methods for providing energy for a medical procedure. More particularly, the present disclosure relates to providing power to a bipolar energy controller.

BACKGROUND

Electrosurgical instruments have become widely used by surgeons to perform surgical procedures. Electrosurgery involves the application of thermal and/or electrical energy to cut, dissect, ablate, coagulate, cauterize, seal or otherwise treat biological tissue during a surgical procedure. Electrosurgery is typically performed using an electrosurgical generator operable to produce energy and a surgical instrument adapted to apply energy to a patient during electrosurgical procedures. Electrosurgery can be performed using either a monopolar or a bipolar instrument. A monopolar instrument applies energy to a patient but does not operate to receive return energy from the patient. In contrast, a bipolar instrument applies energy to a patient and receives return energy from the patient.

Procedures performed with bipolar instruments use electrosurgical generators that generate and provide energy having characteristics specific to the needs of the procedure being performed. The energy will generally include a specified shape, frequency, period, duty cycle, amplitude, and/or phase, among other characteristics. Energy generated to carry out surgical procedures using a bipolar instrument is commonly referred to as bipolar energy.

There exist several commercially available electrosurgical generators configured to generate bipolar energy. However, the existing generators provide a limited array of bipolar energy and thus can only be used in the performance of a limited variety of electrosurgical procedures. There is continued interest in improving the control and delivery of electrosurgical energy to improve compatibility and applicability of electrosurgical energy to a greater variety of electrosurgical procedures.

SUMMARY

The present disclosure provides a power device. The power device includes at least one connector configured to couple to an electrosurgical generator and to receive electrosurgical energy from the electrosurgical generator, a rectifier configured to electrically couple to the at least one connector and to provide rectified energy based on at least a portion of the electrosurgical energy, an energy storage device configured to store at least a portion of the rectified energy, and a bipolar energy controller configured to be powered by the energy storage device and to control providing of an output bipolar energy.

In embodiments of the power device, the electrosurgical energy received from the electrosurgical generator includes a bipolar energy. In embodiments, the controller controls the output bipolar energy to have at least one characteristic different from the bipolar energy received from the electrosurgical energy.

In embodiments, the power device further includes a switch electrically coupled to a monopolar connector, a bipolar connector and the rectifier. The switch is configured to toggle between a monopolar position in which the switch couples the rectifier to the monopolar connector and a bipolar position in which the switch couples the rectifier to the bipolar connector.

In one aspect of the present disclosure, the switch is positioned in the monopolar position when the least one connector first receives the electrosurgical energy. In embodiments, the switch is configured to toggle to the bipolar position based on the amount of energy stored in the energy storage device. In other embodiments of the power device, the switch is configured to toggle to the bipolar position after the switch has been in the monopolar position for a predetermined amount of time.

In other embodiments of the power device, the switch is configured to toggle to the bipolar position when the amount of energy stored in the energy storage device is greater than a threshold. In another embodiment, the switch is configured to toggle to the monopolar position when the amount of energy stored in the energy storage device is less than a threshold.

In other embodiments, the energy storage device receives and stores at least a portion of the electrosurgical energy when the switch is in the bipolar position.

In embodiments of the power device, the controller is coupled to the at least one connector and determines at least one of a frequency or an amplitude of the bipolar energy of the electrosurgical energy.

The present disclosure provides a method of controlling the delivery of bipolar energy. The method includes receiving monopolar energy from an electrosurgical generator, rectifying at least a portion of the monopolar energy to provide a rectified energy, charging an energy storage device with at least a portion of the monopolar energy, detecting bipolar energy from the electrosurgical generator, and powering a controller using the energy storage device, where the controller is configured to control the providing of an output bipolar energy that has at least one characteristic different from the bipolar energy. In embodiments, the method includes detecting at least one of the amplitude, phase, or frequency of the first bipolar energy.

In embodiments, the method includes receiving at least a portion of the bipolar energy from the electrosurgical generator at the energy storage device. In embodiments, the method includes rectifying at least a portion of the bipolar energy.

In one aspect of the present disclosure, the method includes switching between rectifying at least a portion of the monopolar energy and rectifying at least a portion of the bipolar energy. In embodiments, the method switches to rectifying at least a portion of the bipolar energy when the energy stored on the energy storage device is greater than a threshold energy level. In another embodiment, the method switches to rectifying at least a portion of the bipolar energy rectifying at least a portion of the monopolar energy has occurred for a predetermine amount of time.

In embodiments, the method includes charging the energy storage device with at least a portion of the bipolar energy.

In embodiments, the method includes decreasing the monopolar energy to a stepped-down monopolar energy and rectifying at least a portion of the stepped-down monopolar energy to provide the rectified energy.

Any of the above aspects of the present disclosure, to the extent consistent, may be combined without departing from the scope of the present disclosure.

BRIEF DESCRIPTION OF THE DRAWINGS

Various aspects of the present disclosure are described hereinbelow with reference to the drawings, wherein.

DETAILED DESCRIPTION

The disclosed technology relates to systems, apparatuses, and methods for providing bipolar energy for an electrosurgical procedure. The disclosed systems, apparatuses, and methods receive energy from electrosurgical generators that have a limited selection of bipolar energy characteristics and control the delivery of different bipolar energies that are usable in considerably more electrosurgical procedures. As used herein, the terms "couple" or "electrically couple" mean that one component is in electrical communication with another component such that at least a portion of electrical energy from one component passes to another component, whether directly or through one or more intermediate components.

Figure 1:
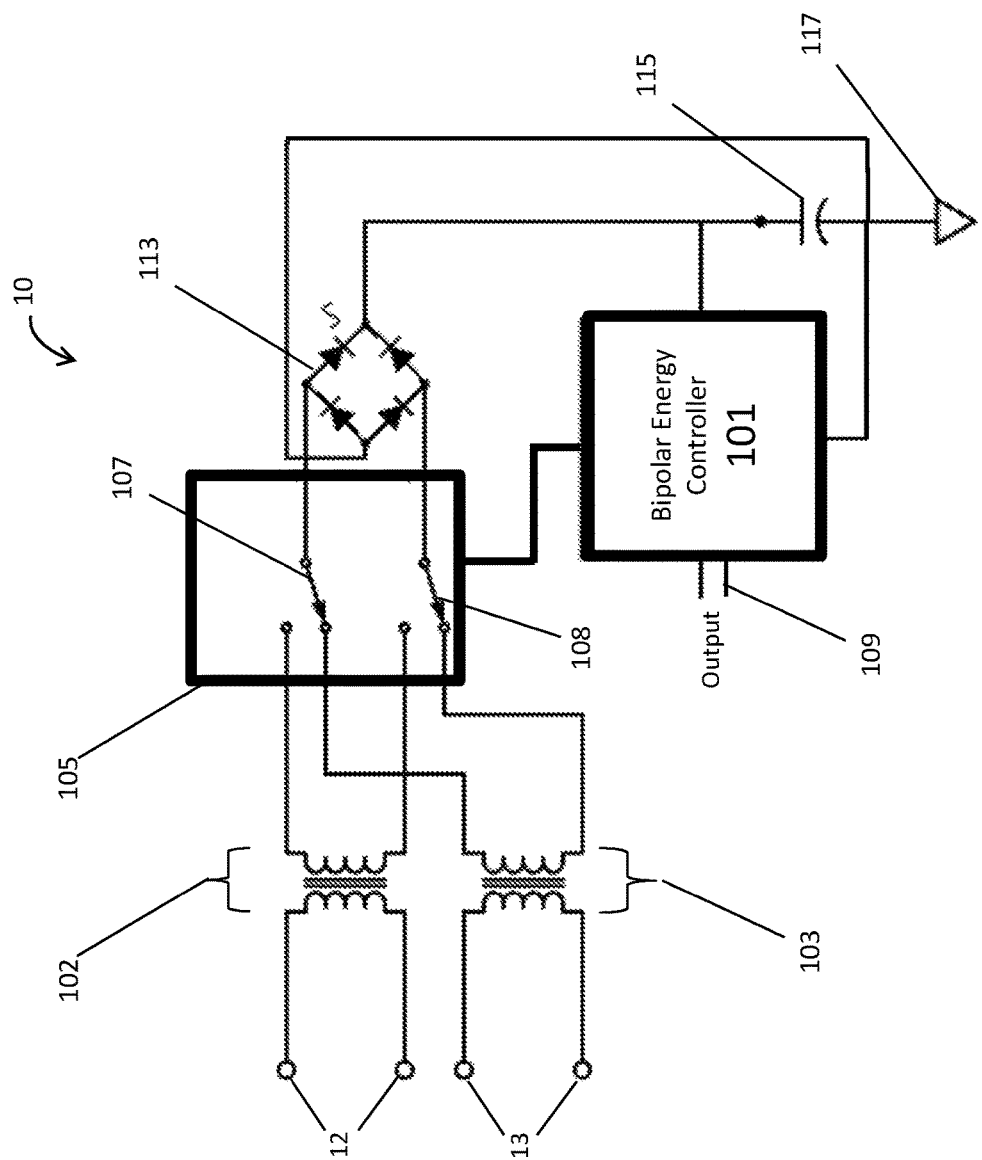
FIG. 1 shows an exemplary circuitry interface for coupling to an electrosurgical generator.

With references to FIG. 1, there is shown a schematic diagram of a circuitry interface 10 that includes monopolar nodes 12 and bipolar nodes 13 that are configured to couple to an electrosurgical generator (not shown). In embodiments, these nodes can be implemented as a plug that is designed to connect to a monopolar and/or a bipolar port of an electrosurgical generator. Once the electrosurgical generator is activated, the monopolar and bipolar nodes 12, 13 can receive monopolar and bipolar energy, respectively, from the generator. The terms "monopolar energy" and "bipolar energy" have meanings that are well-established in the art. The frequency of the energy produced by the electrosurgical generator can vary, but, in various embodiments, can range from 200 kHz to 3.3 MHz. In other embodiments, the frequencies of the electrosurgical energy can be outside of those ranges as well.

The circuitry interface 10 includes two transformers 102 and 103 that together include two sets of primary and secondary windings. One transformer 102 is connected to the monopolar nodes 12, and the other transformer 103 is connected to the bipolar nodes 13. The electrosurgical generator, to which circuitry interface 10 is coupled, provides monopolar energy to the primary winding of transformer 102 and provides bipolar energy to the primary winding of transformer 103 Through induction, the monopolar energy and bipolar energy are coupled to the secondary windings of transformer 102 and transformer 103, respectively. In various embodiments, the transformers 102, 103 can be isolation transformers that electrically protect components on the secondary side of the transformers 102, 103 from electrical faults of the electrosurgical generator. For example, transformers 102 and 103 can prevent electrical surges and other electrical faults at the electrosurgical generator from reaching and harming the secondary side of the circuitry interface 10.

In various embodiments, the transformers 102, 103 are step-down transformers that decrease the voltage at the monopolar and bipolar nodes 12, 13, such that a lower voltage appears at the secondary windings of the transformers 102, 103. In various embodiments, the step-down factor can be in the range of 10 to 100. For example, if the peak-to-peak voltage at the primary winding of the transformers 102, 103 is 400 V peak-to-peak, then with a step-down factor of 10, the voltage at the secondary side of the transformers would be 40 V peak-to-peak. In various embodiments, the step-down factor can be lower than 10 or greater than 100. In various embodiments, the transformers 102, 103 can be step-down as well as isolation transformers.

Monopolar energy and bipolar energy at the secondary side of transformers 102 and 103, respectively, are received at switching circuitry 105. Switching circuitry 105 in FIG. 1 includes two switches 107, 108. Switches 107 and 108 connect to either the secondary winding of transformer 102 or the secondary winding of transformer 103. In embodiments, switches 107 and 108 are designed to switch in tandem with each another such that they both connect to the secondary winding of transformer 102 or both connect to the secondary winding of transformer 103.

In embodiments, interface circuitry 10, when first receiving energy from the electrosurgical generator, can operate with switches 107 and 108 connected to the secondary winding of transformer 102 (position not shown in FIG. 1), which will be referred to herein as "monopolar position." From there, switches 107 and 108 may be switched in a number of different manners. In embodiments, switches 107 and 108 may switch from the monopolar position to being connected to the secondary winding of transformer 103, which will be referred to herein as "bipolar position" (shown in FIG. 1). As will be discussed later herein, switches 107, 108 can alternate between the monopolar position and the bipolar position based on an energy level of the energy storage device 115. As used herein, a switch "position" refers to connectivity and includes connectivity established by a mechanical switch or connectivity established by an electrical switch, such as a field-effect transistor.

In one embodiment, switching circuitry 105 may include control circuitry that determines a length of time that energy has passed through switches 107 and 108 and, when a predetermined amount of time has lapsed, the control circuitry may cause switches 107 and 108 to switch from the monopolar position to the bipolar position or from the bipolar position to the monopolar position. Other ways of controlling switching of switches 107 and 108 are contemplated and include, for example, control based on errors or fault conditions, user inputs, energy characteristics, and/or measured voltage, current, impedance, temperature, or another measurable quantity in circuitry interface 10, in the tissue of a patient on which an electrosurgical procedure is being performed, or in any device or component shown or described in the present disclosure.

Switching circuitry 105 may include other components not illustrated in FIG. 1, including, for example, a memory, a microprocessor, a clock circuit, sensors, control circuitry, and/or hardwired logic circuits. A person skilled in the art will recognize the circuits and components that could be used in the switching circuitry 105 to provide the operations described herein, including, for example, off-the-shelf components that perform switching operations according to the various types of switch control described above or according to other types of switch control that are within the scope of the disclosed technology.

In one aspect of the present disclosure, the switches 107, 108 are connected to a rectifier 113. Depending on the position of switches 107 and 108, rectifier 113 receives energy conveyed through either the monopolar nodes 12 or the bipolar nodes 13. In either case, the energy received by rectifier 113 can be AC energy. Rectifier 113 converts the AC energy to DC energy. Rectifier 113 is shown as a full-wave bridge rectifier comprised of diodes. In other embodiments, rectifier 113 can be another type of full-wave rectifier or can be a half-wave rectifier.

The rectifier 113 is connected to an energy storage device 115 and a bipolar energy controller 101. The energy from the rectifier 113 charges the energy storage device 115, which powers the bipolar energy controller 101. As shown in FIG. 1, the energy storage device 115, the rectifier 113, and the bipolar energy controller 101 are all connected to a common, virtual ground 117.

The energy storage device 115 will now be described. The energy storage device 115 is illustrated as a capacitor, but in other embodiments, can be another type of energy storage device component, circuit, or device. With continuing reference to FIG. 1, the DC energy provided by the rectifier 113 has many energy sub-components, including a DC offset sub-component and AC sub-components of different frequencies and magnitudes. The DC offset component operates to charge the energy storage device capacitor 115. As is well known, the charge across a capacitor is $Q_c = CV_c$, where C is the capacitance of the capacitor and $V_c$ is the voltage across the capacitor. When the DC offset sub-component $V_{dc}$ of the output of the rectifier 113 charges the capacitor 115, the amount of charge across the capacitor 115 will approach $Q_c = CV_{dc}$. The AC sub-components operate to charge and discharge the energy storage device capacitor 115 to varying degrees, which creates a ripple in the level of charge $Q_c$ stored in the energy storage device capacitor 115 but does not completely discharge the energy storage device capacitor 115. Higher frequency AC sub-components have a lesser effect on the ripple due to the impedance at higher frequencies: $Z_c = (j\omega C)^{-1}$. That is, any AC current through the capacitor on account of the higher frequency sub-components will correspond to very small AC voltage across the capacitor, thereby corresponding to very small charge ripple across the capacitor. In this manner, the output of rectifier 113 operates to charge the energy storage device capacitor 115.

In embodiments, the voltage across the energy storage device 115 is +5V. In one embodiment, the voltage across energy storage device 115 is +3.3V. In embodiments, the transformers 102, 103 can have step-down factors that enable the voltage across the energy storage device 115 to achieve the desired voltage. In embodiments, energy from either the monopolar nodes 12 or the bipolar nodes 13 can operate to charge the energy storage device 115. In embodiments, energy from the monopolar nodes 12 can operate to charge the energy storage device 115, but energy from the bipolar nodes may not operate to charge the energy storage device. In embodiments, the step-down factor of the transformers 102, 103 can be chosen based on whether the rectifier 113 is a full-wave rectifier or a half-wave rectifier. For example, to produce approximately 30 watts of power at approximately 350 volts for cutting and coagulation procedures, the transformers 102, 103 may be chosen to provide a 10:1 step-down ratio As mentioned above, the energy storage device 115 powers the bipolar energy controller 101. The bipolar energy controller 101 can be a microcontroller, a digital signal processor, a programmable logic device, an Application Specific Integrated Circuit (ASIC), or custom digital and/or analog circuitry, or a combination of such devices. The bipolar energy controller 101 controls the providing of a bipolar energy signal according to a user selection or according to pre-determined information, which will be described in more detail in connection with FIGS. 4-8. In accordance of one aspect of the present disclosure, the bipolar energy controller 101 operates to detect certain characteristics of the bipolar energy provided through the bipolar nodes 13. In the configuration of FIG. 1, the bipolar energy controller 101 can detect the frequency of the bipolar energy provided at the bipolar nodes 13. In particular, when the switches 107, 108 are in the bipolar position, the rectifier 113 receives the stepped-down AC bipolar energy from transformer 103 and generates DC energy that rises and falls with twice the frequency of the bipolar energy, while never dropping below 0. Therefore, bipolar energy controller 101 may detect the frequency of the DC energy from the rectifier 113 in order to determine the frequency of the bipolar energy provided by the electrosurgical generator (not shown). Knowing the frequency of the bipolar energy provided by the electrosurgical generator, the bipolar energy controller 101 can control the providing of different bipolar energy having different characteristics, as will be described below. The bipolar energy controller 101 can provide control signals at an output connection 109.

With continuing reference to FIG. 1, the position of switches 107, 108 can be controlled based on the energy level in the energy storage device 115. As the energy storage device 115 powers the bipolar energy controller 101, the bipolar energy controller may draw current from the energy storage device 115. In doing so, the voltage $V_c$ across the energy storage device capacitor 115 will decrease based on the relationship $$-i_c = C \cdot \left(-\frac{dV_c}{dt}\right).$$

Thus, me energy storage device 115 will need to be recharged.

In one aspect of the present disclosure, the switches 107, 108 may be in the monopolar position until the energy storage device 115 charges to an energy level sufficient for powering the functions of bipolar energy controller 101, such as a desired voltage level threshold. In embodiments, the voltage level threshold can be +5V or +3.3V, for example. When the voltage level threshold is detected across energy storage device 115, the switches 107, 108 can switch to the bipolar position, so that the bipolar energy controller 101 can detect characteristics of the bipolar energy provided at the bipolar nodes 30. In embodiments, when the switches 107, 108 are in the bipolar position, the rectified energy from rectifier 113 can charge the energy storage device 115 to some degree. When the energy level of energy storage device 115 drops and becomes insufficient for powering the functions of bipolar energy controller 101, the switches 107, 108 can switch back to the monopolar position to charge the energy storage device 115. In embodiments, the energy level can be insufficient when the voltage drops below another threshold, such as +4.5V or +3.0V, for example. In embodiments, the position of switches 107, 108 can be controlled by the bipolar energy controller 101. In embodiments, the position of switches 107, 108 can be controlled by control circuitry (not shown) in the switching circuitry 105. In further embodiments, the switches 107, 108 may be in the monopolar position for a predetermined amount of time.

Figure 2:
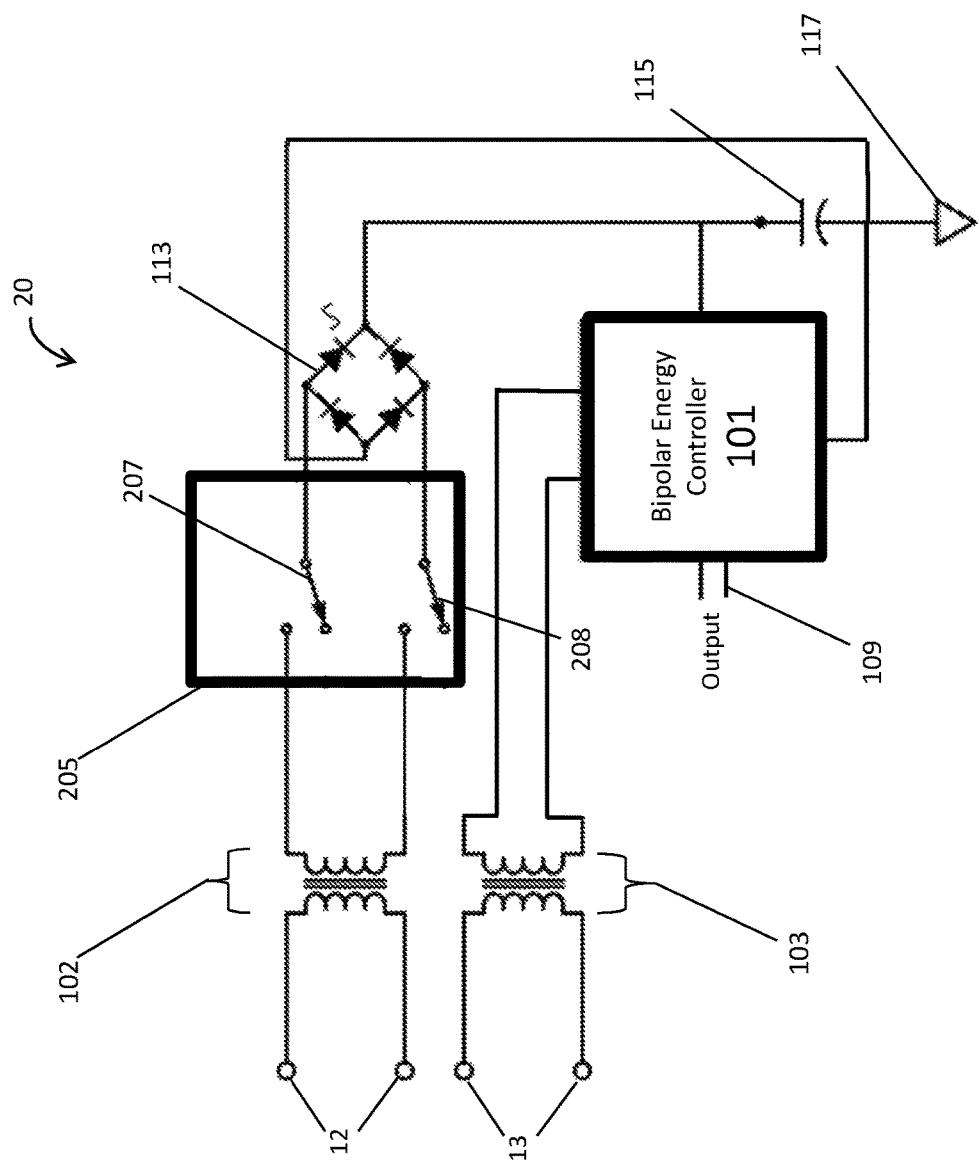
FIG. 2 shows another exemplary circuitry interface for coupling to an electrosurgical generator.

With reference to FIG. 2, there is shown a diagram of another embodiment of a circuitry interface. Circuitry interface 20 functions the same way as circuitry interface 10 of FIG. 1 in many aspects and includes many of the same components. However, instead of the bipolar nodes 13 coupling to switching circuitry 105 across transformer 103 as in FIG. 1, the bipolar nodes 13 couple to the bipolar energy controller 101 directly through the transformer 103. Only the monopolar nodes 12 are coupled to the switching circuitry 205. Switching circuitry 205, similar to switching circuitry 105 of FIG. 1, includes two switches 207 and 208. Switches 207 and 208, rather than switching between bipolar and monopolar positions as in FIG. 1, switch between a monopolar position and an open position. When switches 207, 208 are in a monopolar position, the interface circuitry 20 operates to charge the energy storage device 115 in the same way as circuitry interface 10. In FIG. 2, when the voltage across energy storage device 115 reaches a voltage level threshold, the switches 207, 208 can switch to the open position. When the voltage across energy storage device 115 drops below another voltage level threshold, the switches 207, 208 can switch back to the monopolar position.

In FIG. 2, because the bipolar energy controller 101 is connected directly to the secondary winding of transformer 103, bipolar algorithm controller 101 receives a stepped-down version of the bipolar energy provided from the electrosurgical generator (not shown) to the bipolar nodes 13. Bipolar energy controller 101 may detect the frequency of the bipolar energy through this direct connection. Knowing the frequency of the bipolar energy provided by the electrosurgical generator, the bipolar energy controller 101 can control the providing of different bipolar energy having different characteristics, as will be described below. The bipolar energy controller 101 can provide control signals at an output connection 109.

Figure 3:
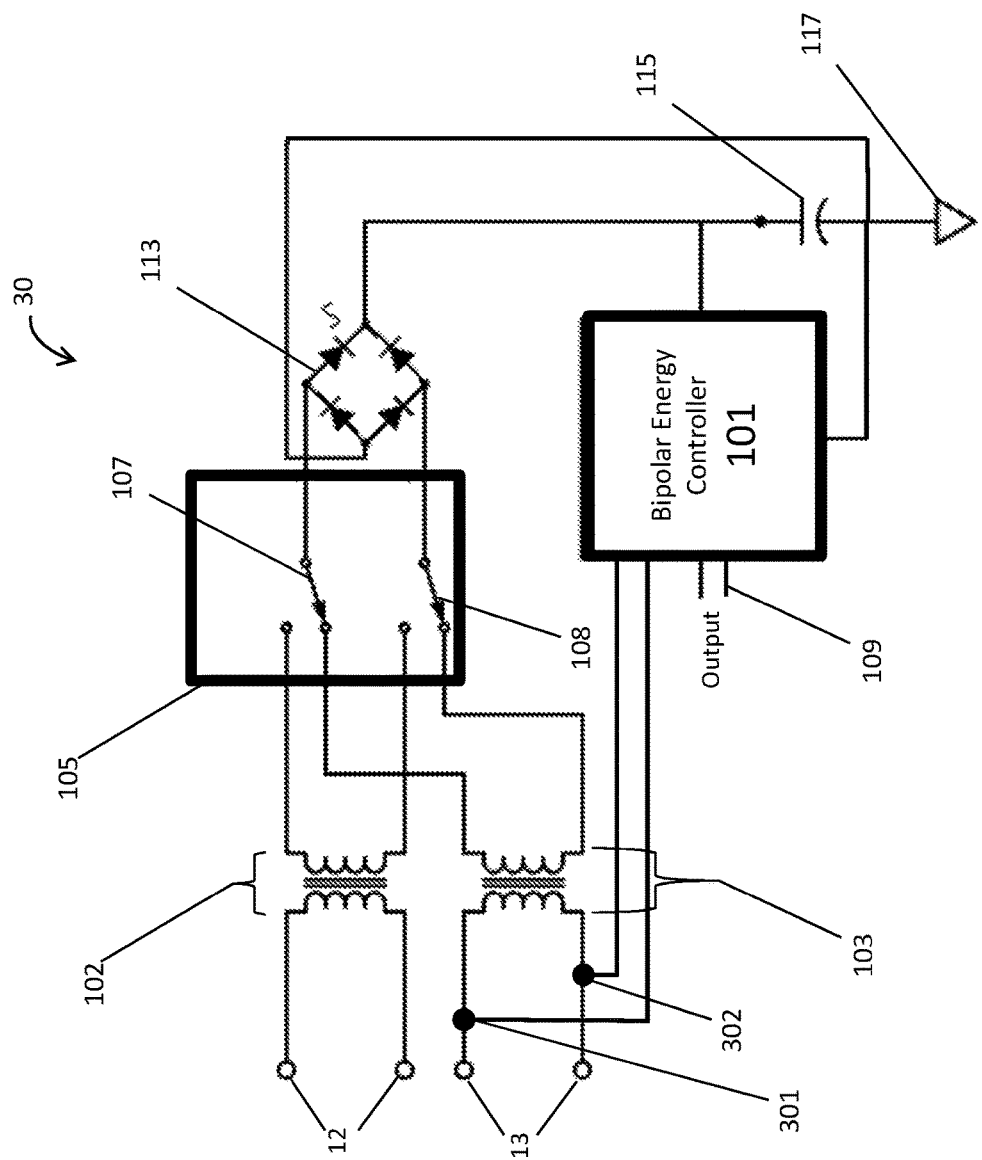
FIG. 3 shows yet another exemplary circuitry interface for coupling to an electrosurgical generator.

Referring now to FIG. 3, there is shown a diagram of another embodiment of a circuitry interface. Circuitry interface 30 functions the same way as circuitry interface 10 of FIG. 1 in many respects and includes many of the same components. Unlike circuitry interface 10 of FIG. 1 and circuitry interface 20 of FIG. 2, the bipolar nodes 301, 302 are coupled directly to bipolar energy controller 101. The direct connection of the bipolar nodes 301, 302 to the bipolar energy controller 101 allows the bipolar energy controller 101 to detect characteristics of the bipolar energy provided by the electrosurgical generator (not shown), including frequency, magnitude, phase, duty cycle, among other things. Knowing the characteristics of the bipolar energy provided by the electrosurgical generator, the bipolar energy controller 101 can control the providing of different bipolar energy having different characteristics, as will be described below. The bipolar energy controller 101 can provide control signals at an output connection 109.

Figure 4:
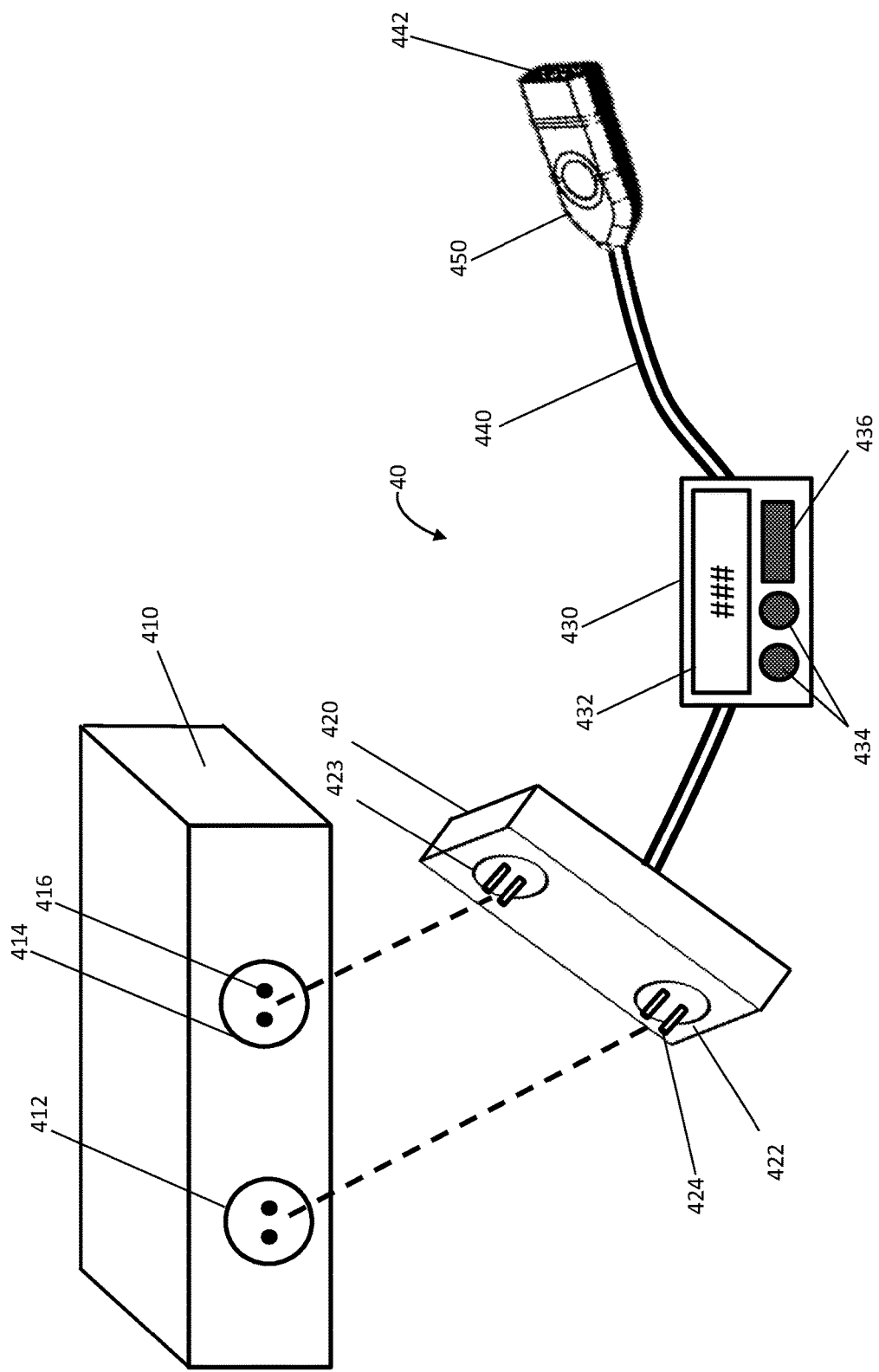
FIG. 4 shows an exemplary electrosurgical adaptor according to aspects of the present disclosure.

With reference to FIG. 4, there is shown a system that includes an electrosurgical adapter 40 which is configured to couple to electrosurgical generator 410. Electrosurgical generator 410 can be any generator that provides monopolar and bipolar energy for surgical procedures, such as, but not limited to, the Medtronic FORCE FX™ generator. Electrosurgical generator 410 includes a monopolar port 412 and a bipolar port 414, which are designed to connect to an electrosurgical instrument to provide monopolar energy and bipolar energy, respectively. In accordance with aspects of the present disclosure, the monopolar and bipolar nodes in FIGS. 1-3 are configured to connect to the monopolar port 412 and the bipolar port 414, respectively. The arrangement of connector holes 416 for monopolar port 412 and bipolar port 414 shown in FIG. is exemplary. Other connectors and connection configurations are contemplated. For example, in various embodiments, there may be a single receiving hole 416 for each port 412, 414 in order to receive a coaxial or other type of connector prong or there may be three or more receiving holes 416 for each port 412, 414 to accommodate other connections to an electrosurgical treatment instrument or an electrosurgical adapter 40.

Electrosurgical adapter 40 includes generator connector 420, user interface 430, connecting wire 440, and device connector 450. Electrosurgical adapter 40 is configured to receive both bipolar and monopolar electrosurgical energy from electrosurgical generator 410 and to output different bipolar energy at device port 442. The electrosurgical adapter 40 includes a circuitry interface in accordance with the present disclosure, such as one of the circuitry interfaces 10, 20, 30 shown in FIGS. 1-3. Circuitry interface 10, 20, 30 may be located wholly within generator connector 420, user interface 430, connecting wire 440, or device connector 450, or individual components of circuitry interface 10, 20, 30 may be distributed among the generator connector 420, user interface 430, connecting wire 440, or device connector 450.

Generator connector 420 includes monopolar connector 422 and bipolar connector 423. The monopolar connector 422 and bipolar connector 423 are shown with two connector pins 424. Connector pins 424 are designed to be inserted into receiving holes 416. Connector pins 424 of monopolar connector 422 are received by monopolar port 412, and connector pins 424 of bipolar connector 423 are received by bipolar port 414. Once the connector pins 424 are received by receiving holes 416, an electrical connection is created. In one embodiment, the physical connection is achieved through a friction fit. In various embodiments, other types of connections are contemplated.

As with receiving holes 416, the number of connector pins 424 may vary. In one embodiment, the number of connector pins 424 corresponds to the number of receiving holes 416. In other embodiments, the number of connector pins 424 can be less than the number of receiving holes 416.

With continuing reference to FIG. 4, user interface 430 is connected to generator connector 420. User interface 430 includes display 432, toggle buttons 434, and selection button 436. Display 432 displays a status of electrosurgical adapter 40 and can display other information, such as characteristics of the bipolar energy provided by the electrosurgical adaptor 40. Display 432 may further display other useful information to a user to indicate characteristics of the electrosurgical generator, the electrosurgical instrument, or the electrosurgical adapter 40.

Toggle buttons 434 and selection button 436 allow a user to select various options and transition between various views and displays shown on display 432. In embodiments, toggle buttons 434 may allow a user to toggle through bipolar energy settings and selection button 436 may allow the user to select the setting that is displayed. In other embodiments, the selection button 436 can be pressed to cycle through bipolar energy characteristics, such as voltage or magnitude, and the toggle buttons 434 can allow a user to increase or decrease the value of the characteristic that is displayed. The user selections can be used by the bipolar energy controller 101 (FIGS. 1-3) to control the providing of bipolar energy according to the selected settings or characteristics.

Surgical device connector 450 is connected to user interface 430 via connecting wire 440. Surgical device connector 450 is configured to connect to a surgical device (not shown). Surgical device connector 450 includes device port 442 which receives connector pins of a surgical device. Device port 442 operates to transfer bipolar energy to a surgical device.

Figure 5:
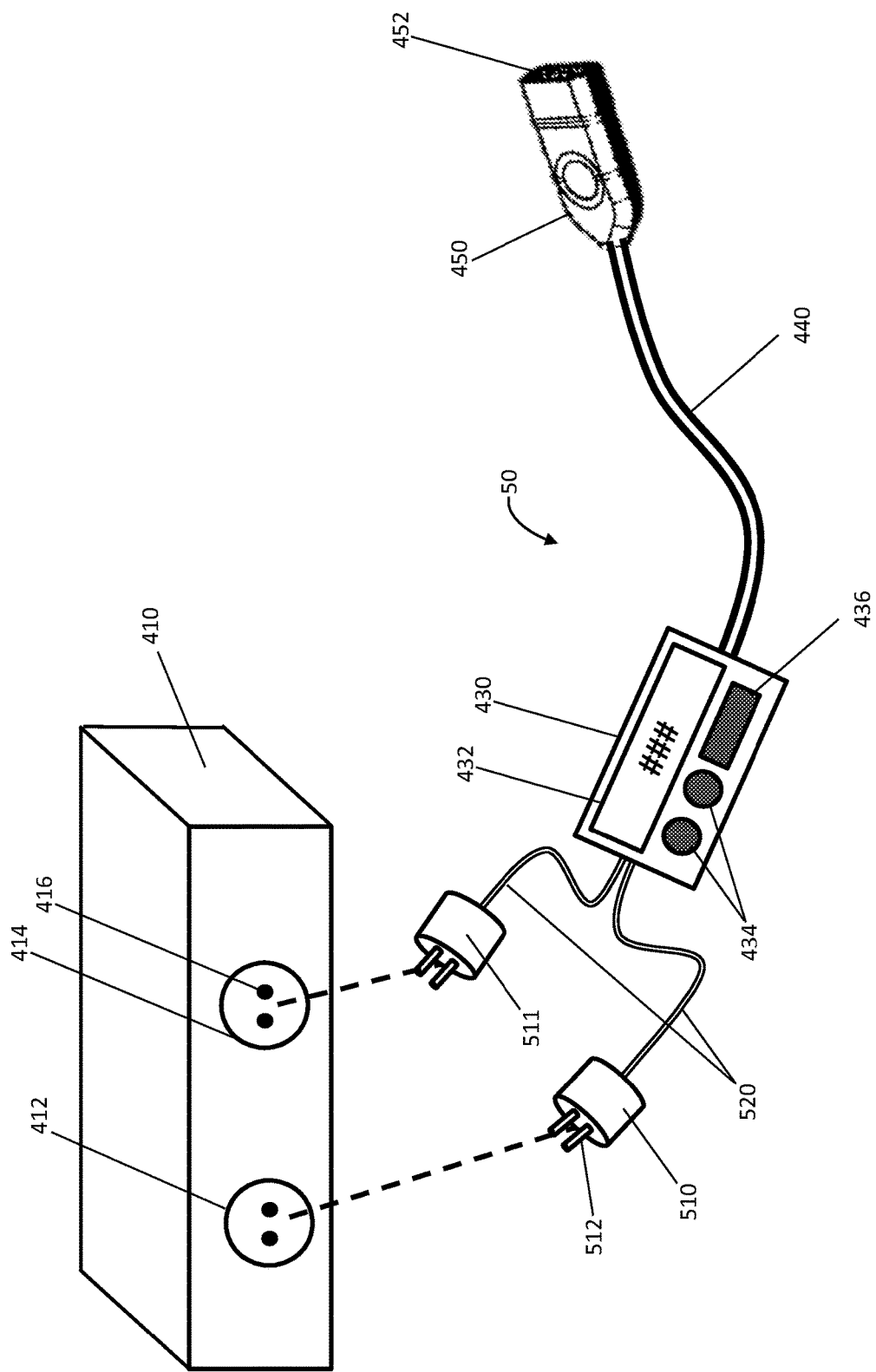
FIG. 5 shows another exemplary electrosurgical adaptor according to aspects of the present disclosure.

Referring now to FIG. 5, there is shown another embodiment of an electrosurgical adapter. Electrosurgical adapter 50 includes many of the same components as the electrosurgical adapter 40 of FIG. 4, including user interface 430, connecting wire 440, and device connector 450. Electrosurgical adaptor 50 differs in that it includes separate monopolar connector 510 and bipolar connector 511, which are connected to user interface 430 by wires 520. Monopolar connector 510 and bipolar connector 511 are configured to connect to generator 410 at monopolar port 412 and bipolar port 414, respectively. By providing separate connectors for the monopolar port 412 and the bipolar port 414, electrosurgical adapter 50 is able to couple to a larger variety of electrosurgical generators.

Monopolar connector 510 and bipolar connector 511 include connector pins 512 configured to plug into receiving holes 416 of the electrosurgical generator 410. In the illustrated embodiment, monopolar connector 510 and bipolar connector 511 each have two connector pins 512. In other embodiments, monopolar connector 510 and bipolar connector 511 may include another number of pins.

Figure 6:
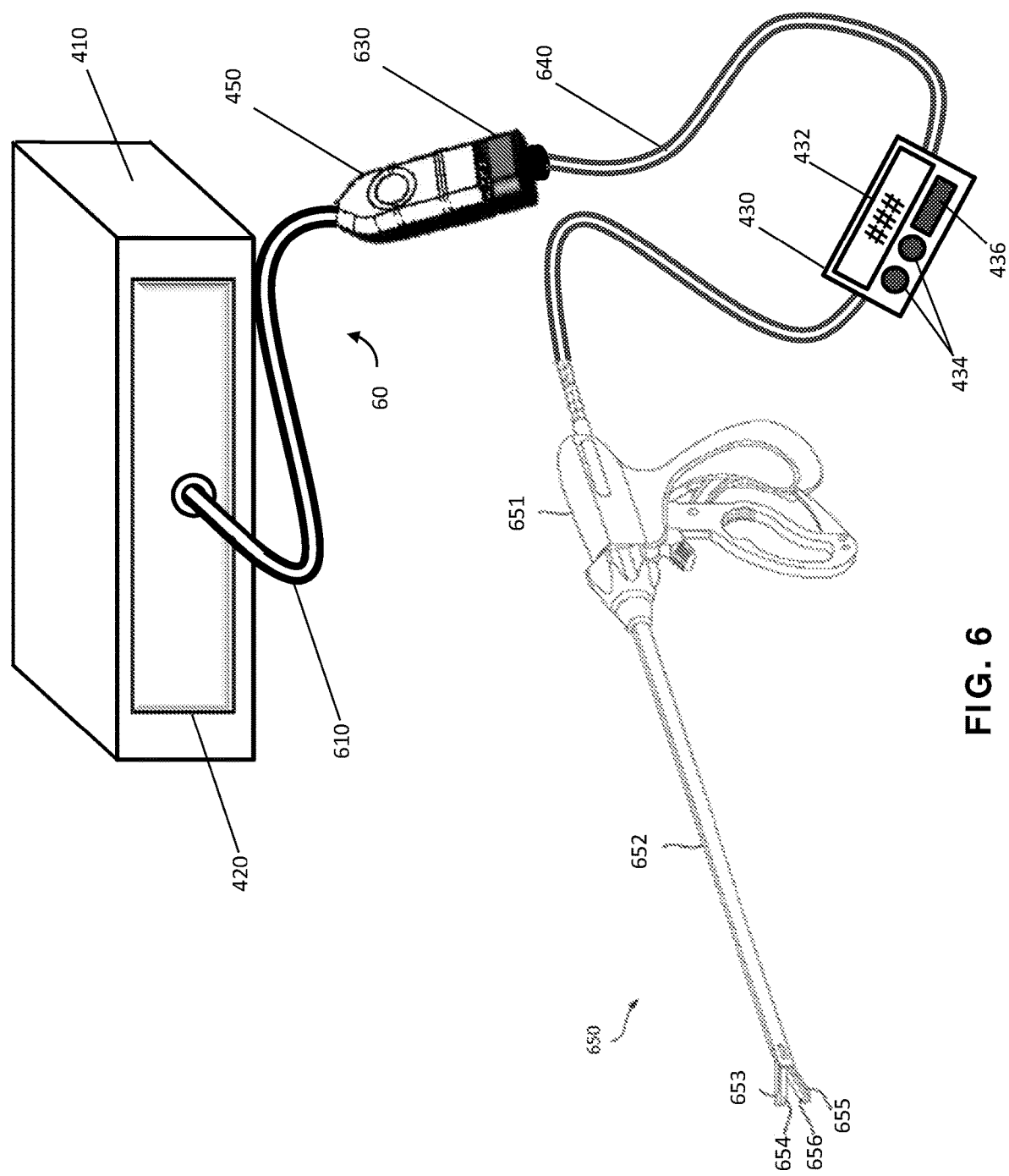
FIG. 6 shows an exemplary electrosurgical generator and an exemplary electrosurgical instrument coupled to the electrosurgical adaptor of FIG. 4.

With reference now to FIG. 6, there is shown another embodiment of an electrosurgical adapter 60. Electrosurgical adapter 60 includes a generator connector 420, a device connector 450, and a connecting wire 610 therebetween. Circuitry interface 10, 20, 30 may be entirely located in generator connector 420 or in device connector 450, or individual components of circuitry interface 10, 20, 30 may be distributed among generator connector 420 and device connector 450. In the embodiment of FIG. 6, electrosurgical adapter 60 does not include a user interface 430. Instead, user interface 430 is part of electrosurgical instrument 650. In various embodiments (not shown), user interface 430 may be part of or embedded in housing 651 of electrosurgical instrument 650.

Electrosurgical instrument 650 is an exemplary bipolar electrosurgical instrument. Electrosurgical instrument 650 can include one or more electrodes 654, 656 for applying electrosurgical energy to the tissue of a patient. The electrosurgical instrument 650 includes a housing 651 and opposing jaw members 653, 655 disposed at a distal end of a shaft 652. The jaw members 653 and 655 have one or more active electrodes 654 and a return electrode 656 disposed therein, respectively. The active electrode 654 and the return electrode 656 are connected to the electrosurgical adapter 60 through cable 640. Electrosurgical instrument 650 is coupled to electrosurgical adapter 60 at plug 630, which connects to device connector 450. Plug 630 can include pins (not shown) configured to plug into device port 442. However, plug 630 and device port 442 may also be coupled in another manner.

Figure 7:
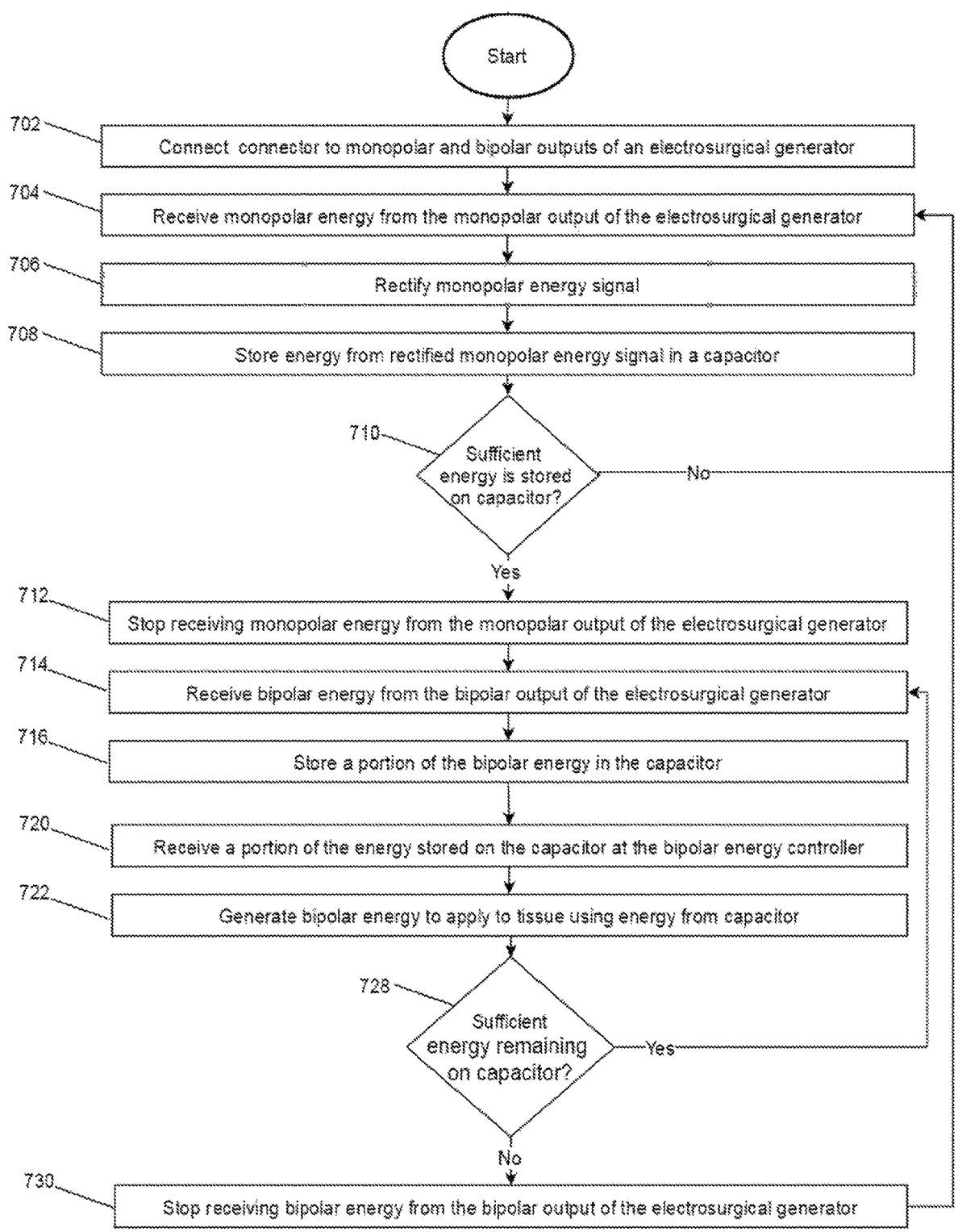
FIG. 7 is a flow chart of a process for receiving energy from an electrosurgical generator and providing bipolar energy.

Turning to FIG. 7, there is shown a flow chart of a process for receiving energy from an electrosurgical generator to charge an energy storage device and for powering a controller that controls the providing of bipolar energy. The process is described herein with reference to FIGS. 1 and 4. However, the process is applicable to any electrosurgical adapter and circuitry interface within the scope of the present disclosure.

The process begins at step 702. At step 702, the electrosurgical adapter 40 including circuitry interface 10 is coupled to monopolar port 412 and bipolar port 414 of electrosurgical generator 410, establishing a connection with the monopolar and bipolar nodes shown in FIG. 1. Once a connection is made, electrosurgical generator 410 is powered on and appropriate settings for outputting monopolar and bipolar energy are selected such that, at step 704, monopolar and/or bipolar energy is received at the monopolar and/or bipolar nodes, respectively. When energy is first received from the monopolar and/or bipolar nodes, switches 107, 108 are in the monopolar position and allow monopolar energy to flow through transformer 102 and reach rectifier 113.

At step 706, the monopolar energy passes through rectifier 113, causing the energy to be rectified. The energy is rectified, for example, using a diode bridge circuit as shown in FIG. 1. Therefore, DC energy is output from the rectifier.

At step 708, at least a portion of the DC energy is stored by energy storage device 115. That is, the charge at energy storage device 115, which may be, for example, a capacitor or battery, increases over time and is preserved.

At step 710, the amount of energy stored by energy storage device 115 is determined. In embodiments, the determination as to the amount of energy stored in energy storage device 115 may be made using a sensor (not shown) configured to measure the voltage across energy storage device 115. In embodiments, a processor (not shown) may be used to determine an amount of time the rectified energy is applied and stored in energy storage device 115 to determine the amount of energy stored. If the energy stored at energy storage device 115 is below a predetermined threshold, steps 704-708 are repeated until the threshold is achieved. Once sufficient energy is achieved, the process continues to steps 712 and 714.

At step 712, switches 107, 108 are toggled to the bipolar position and no longer receive monopolar energy through the transformer 102. At step 714, switches 107, 108 receive bipolar energy through transformer 103. The bipolar energy passes through rectifier 113 and becomes rectified energy, and at step 716, at least a portion of the rectified energy is stored in the energy storage device 115.

At step 720, bipolar energy controller 101 draws a portion of the energy stored on energy storage device 115. The energy drawn from energy storage device 115 may be used by bipolar energy controller 101 to power a processor and/or other components contained within bipolar energy controller 101.

At step 722, bipolar energy controlled by the bipolar energy controller 101 is generated. The bipolar energy is generated according to bipolar energy characteristics and/or settings selected by a user using user interface 430. The bipolar energy controller 101 controls, for example, the frequency and magnitude of the bipolar energy that is generated.

At step 728, energy storage device 115 is monitored to determine the amount of energy stored therein. In embodiments, the monitoring is performed by a processor (not shown) and a sensor (not shown) that measures the energy on energy storage device 115. In embodiments, the monitoring is performed by hardware (not shown) that is configured to respond to particular energy levels. If a predetermined amount of energy is stored on energy storage device 115, the process returns to step 714 and steps 714-722 are repeated.

If the energy stored is below the predetermined threshold, the process proceeds to step 730, at which switches 107, 108 are toggled out of the bipolar position so that bipolar energy from transformer 103 is no longer received. The process returns to step 704, and steps 704-722 are repeated. Once the electrosurgical procedure is deemed complete, the process ends. A physician may determine that the tumor has been sufficiently ablated and end the procedure. In the alternative, bipolar energy controller 101 and/or an external device (not shown), such as a temperature probe or an LCR or ohm meter, may measure a property of the tissue and determine that either a completion condition has been achieved or that an error has occurred. Accordingly, when a completion condition or error condition is achieved, bipolar energy controller 101 and/or an external device (not shown) may halt the illustrated process.

Figure 8:
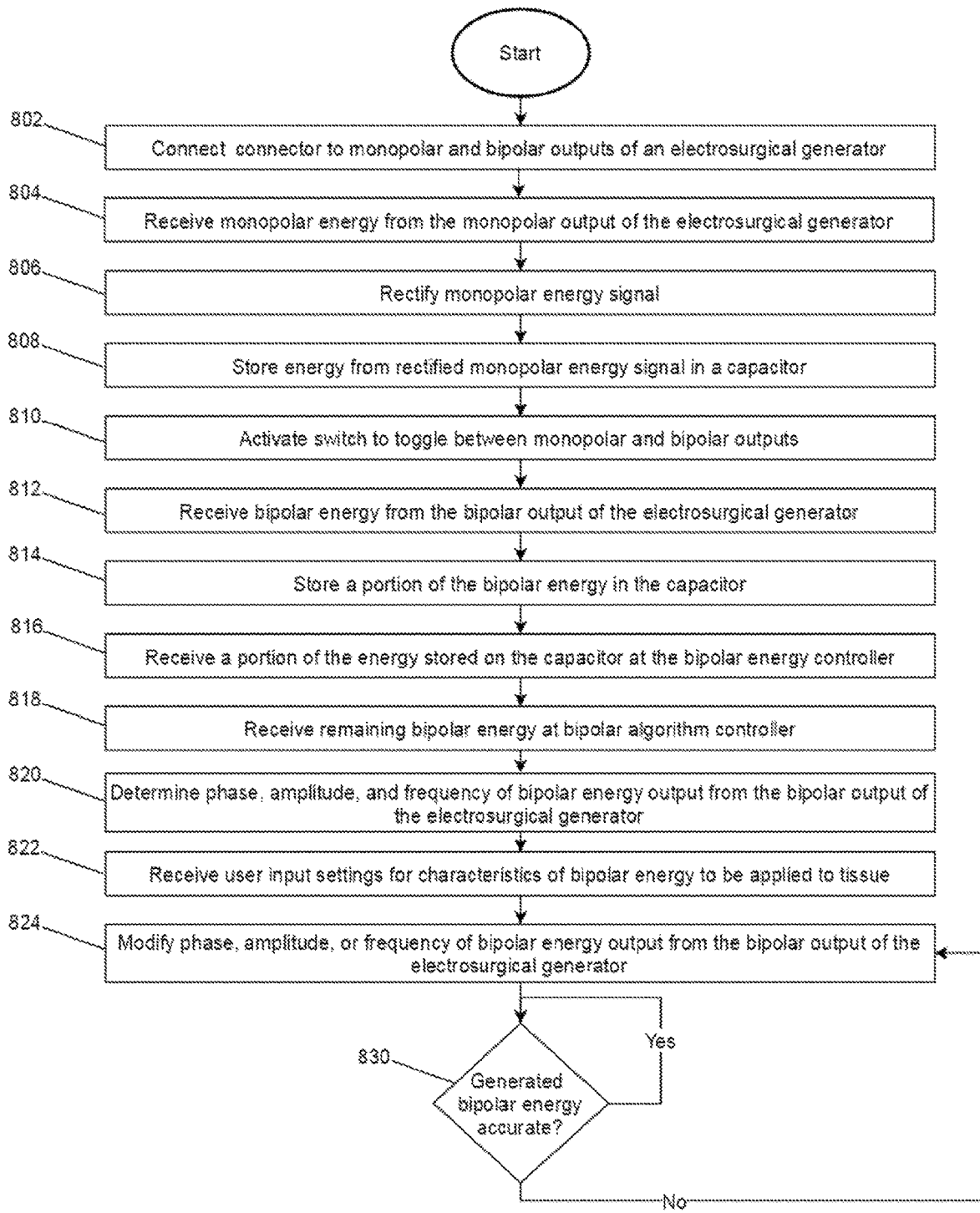
FIG. 8 is a flow chart of another process for receiving energy from an electrosurgical generator and providing bipolar energy.

FIG. 8 shows a flow chart of a process for receiving energy from an electrosurgical generator and controlling the providing of bipolar energy. Steps 802-808 are the same as steps 702-708 of FIG. 7. At step 810, switches 107, 108 are toggled, switching from monopolar position to bipolar position. Then, steps 812-818 are the same as steps 714-716 of FIG. 7.

At step 820, the bipolar energy controller 101 determines a phase, amplitude, and/or frequency of the bipolar energy received at the bipolar nodes 13.

At step 822, a user input is accessed indicating bipolar energy characteristics and/or settings. Bipolar energy controller 101 then applies the user selected characteristics for the bipolar energy to be generated at step 824.

At step 830, bipolar energy controller 101 measures the generated bipolar energy to determine whether it matches the user specified characteristics. If the generated bipolar energy matches the user specified characteristics, the process continues to monitor the generated bipolar energy. If the bipolar energy does not match the user selected characteristics, the process returns to step 824, wherein the bipolar energy controller controls the generated bipolar energy to achieve the user selected characteristics.

What have been described are systems, apparatuses, and methods for charging an energy storage device and powering a controller for controlling the providing of bipolar energy. Embodiments of the present disclosure are located in an electrosurgical adaptor that connects between an electrosurgical generator and an electrosurgical instrument. The embodiments described and illustrated herein are exemplary and do not limit the scope of the present disclosure.

Unless otherwise indicated or apparent from the context, the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also encompassed are database and other data schemas, and any other meta-languages. The present disclosure encompasses languages which are interpreted, compiled, or use both compiled and interpreted approaches. The present disclosure also encompasses compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A power device configured to couple to an electrosurgical generator, the device comprising:
   at least one connector configured to couple to and receive an electrosurgical energy from an electrosurgical generator;
   a rectifier configured to electrically couple to the at least one connector and to provide a rectified energy based on at least a portion of the electrosurgical energy;
   an energy storage device configured to store at least a portion of the rectified energy;
   a controller configured to be powered by the energy storage device and to control providing of an output bipolar energy; and
   a switch electrically coupled to the at least one connector and the rectifier, the at least one connector including a monopolar connector and a bipolar connector, wherein the switch is configured to toggle between a monopolar position in which the switch couples the rectifier to the monopolar connector and a bipolar position in which the switch couples the rectifier to the bipolar connector,
   wherein the controller operates the switch to toggle to the bipolar position based on an amount of energy stored in the energy storage device.

2. The power device according to claim 1, wherein the electrosurgical energy from the electrosurgical generator includes bipolar energy.

3. The power device according to claim 2, wherein the controller is configured to control the output bipolar energy to have at least one characteristic different from the bipolar energy of the electrosurgical energy.

4. The power device according to claim 1, wherein the controller operates the switch to be in the monopolar position when the least one connector first receives the electrosurgical energy.

5. The power device according to claim 1, wherein the controller operates the switch to toggle to the bipolar position when an amount of energy stored in the energy storage device is greater than a threshold.

6. The power device according to claim 1, wherein the controller operates the switch to toggle to the monopolar position when the amount of energy stored in the energy storage device is less than a threshold.

7. The power device according to claim 1, wherein the controller operates the switch to toggle to the bipolar position after the switch has been in the monopolar position for a predetermined amount of time.

8. The power device according to claim 1, wherein the energy storage device receives and stores at least a portion of the electrosurgical energy when the switch is in the bipolar position.

9. The power device according to claim 3, wherein the controller is coupled to the at least one connector and determines at least one of a frequency or an amplitude of the bipolar energy of the electrosurgical energy.

10. A method of controlling an electrosurgical generator, the method comprising:
receiving monopolar energy from an electrosurgical generator;
rectifying at least a portion of the monopolar energy to provide a rectified energy;
charging an energy storage device with at least a portion of the rectified energy;
detecting bipolar energy from the electrosurgical generator;
powering a controller using the energy storage device, the controller configured to control an output bipolar energy that has at least one characteristic different from the bipolar energy;
receiving at least a portion of the bipolar energy from the electrosurgical generator at the energy storage device;
rectifying at least a portion of the bipolar energy;
switching between rectifying at least a portion of the monopolar energy and rectifying at least a portion of the bipolar energy; and
switching to rectifying at least a portion of the bipolar energy when an energy stored on the energy storage device is greater than a threshold energy level.

11. The method according to claim 10, further comprising charging the energy storage device with at least a portion of the bipolar energy.

12. The method according to claim 10, further comprising decreasing the monopolar energy to a stepped-down monopolar energy, wherein rectifying at least a portion of the monopolar energy includes rectifying the stepped-down monopolar energy to provide the rectified energy.

13. The method according to claim 12, wherein detecting the bipolar energy includes detecting at least one of amplitude, phase, or frequency of the bipolar energy.

14. A method of controlling an electrosurgical generator, the method comprising:
receiving monopolar energy from an electrosurgical generator;
rectifying at least a portion of the monopolar energy to provide a rectified energy;
charging an energy storage device with at least a portion of the rectified energy;
detecting bipolar energy from the electrosurgical generator;
powering a controller using the energy storage device, the controller configured to control an output bipolar energy that has at least one characteristic different from the bipolar energy;
receiving at least a portion of the bipolar energy from the electrosurgical generator at the energy storage device;
rectifying at least a portion of the bipolar energy;
switching between rectifying at least a portion of the monopolar energy and rectifying at least a portion of the bipolar energy; and
switching to rectifying at least a portion of the bipolar energy when rectifying at least a portion of the monopolar energy has occurred for a predetermined amount of time.

* * * * *